United States Patent [19]

Katsuki

[11] Patent Number: 4,970,160

[45] Date of Patent: Nov. 13, 1990

[54] GENE FOR CORN PHOSPHOENOLPYRUVATE CARBOXYLASE

[75] Inventor: Hirohiko Katsuki, Kyoto, Japan

[73] Assignee: Sumitomo Chemical Company, Limited, Osaka, Japan

[21] Appl. No.: 899,001

[22] Filed: Aug. 22, 1986

[30] Foreign Application Priority Data

Aug. 23, 1985 [JP] Japan .................. 60-186181

[51] Int. Cl.$^5$ ............... C12N 9/88; C12N 15/60; C12N 15/70
[52] U.S. Cl. ............... 435/232; 435/252.33; 435/320
[58] Field of Search ............ 435/172.3, 70, 253, 435/68, 170, 320, 183, 232; 536/27; 935/14, 23, 27, 30

[56] References Cited

PUBLICATIONS

Hudspeth et al., Proc. Natl. Acad. Sci. vol. 83 (May 1986) pp. 2884–2888.
K. Uedan et al, Chem. Abstracts, vol. 85, No. 74072b, p. 212 (1976).
J. Mares et al, Chem. Abstracts, vol. 91, No. 136056j, p. 247 (1979).
T. Nelson et al, Chem. Abstracts, vol. 100, No. 100089n, p. 372 (1984).
T. Kodaki et al, J. of Biochem., vol. 97, pp. 533–539 (Feb. 1985).
W. L. Millet et al, Drug Development Research, vol. 1, pp. 435–454 (1981).
K. Izui et al, Nucleic Acids Research, vol. 14, No. 4, pp. 1615–1628 (Feb. 14, 1986).
F. Katagiri et al, Gene, vol. 38, pp. 265–269 (1985).
N. Fujita et al, Journal of Biochemistry, vol. 95, No. 4, pp. 909–916 (1984).
N. Sabe et al, Gene, vol. 31, pp. 279–283 (1984).
Y. S. Nasyrov, Chem. Abstracts, vol. 89, No. 39536h, p. 291 (1978).
Y. S. Nasyrov, Chem. Abstracts, vol. 96, No. 82914v, p. 358 (1982).
D. N. Moss, Chem. Abstracts, vol. 87, No. 130430x, p. 351 (1977).
Z. Hanna et al, Gene, vol. 30, No. 1–3, pp. 247–250 (Oct. 1984).
K. A. Barton et al, Science, vol. 219, pp. 671–676 (Feb. 11, 1983).
A. D. Riggs et al, American Journal of Human Genetics, vol. 31, pp. 531–538 (1979).

*Primary Examiner*—Richard A. Schwartz
*Assistant Examiner*—Richard Lebovitz
*Attorney, Agent, or Firm*—Birch, Stewart, Kolasch & Birch

[57] ABSTRACT

A DNA sequence which encodes for a biologically active corn phosphoenolpyruvate carboxylase is disclosed. A recombinant plasmid vector containing the DNA sequence, a microorganism transformed with the vector, and the carboxylase expressed by the organism are also provided.

3 Claims, 12 Drawing Sheets

Fig.1-1
Frame 3

```
CGAGTACGA TGCGCTGCTCGTCGACCGGCTTCCTCAACATCCTTCAGGACCTTCCACGGGCCT      62
 E  Y  D   A  L  L  V  D  R  F  L  N  I  L  Q  D  L  H  G  P          20

AGCCTTCGCGAATTTGTCCAGGAGTGCTACGAGGTATCGGCCGACTACGAGGGCAAAGGA         122
 S  L  R  E  F  V  Q  E  C  Y  E  V  S  A  D  Y  E  G  K  G           40

GACACGACGAAGCTGGGCGAGCTCGGGGCCAAGCTCACGGGGCTGGCCCCTGCCGACGCC         182
 D  T  T  K  L  G  E  L  G  A  K  L  T  G  L  A  P  A  D  A           60

ATCCTCGTGGCGAGCTCCATCCTGCACATGCTCAACCTCGCCAACCTGGCCGAGGAGGTG         242
 I  L  V  A  S  S  I  L  H  M  L  N  L  A  N  L  A  E  E  V           80

CAGATCGCGCACCGCCGCCGCAACAGCAAACTCAAGAAAAAGGTGGCTTCGCCGACGAAGGC      302
 Q  I  A  H  R  R  R  N  S  K  L  K  K  K  G  G  F  A  D  E  G       100

TCCGCCACCACCGAGTCCGACATCGAGGAGACGCTCAAGCGCCTCGTGTCCGAGGTCGGC         362
 S  A  T  T  E  S  D  I  E  E  T  L  K  R  L  V  S  E  V  G          120
```

Fig. 1-2

```
AAGTCCCCCGAGGAGGTGTTCGAGGCGCTCAAGAACCAGACCGTCGACCTCGTCTTCACC    422
 K  S  P  E  E  V  F  E  A  L  K  N  Q  T  V  D  L  V  F  T     140

GCGCATCCCACGCAGTCCGCCCGCTCGCTCCTGCAGAAAAACGCGAGGATCCGGAAT        482
 A  H  P  T  Q  S  A  R  R  S  L  L  Q  K  N  A  R  I  R  N     160

TGTCTGACCCAGCTGAATGCCAAGGACATCACTGACGACGACAAGCAGGAGCTCGATGAG    542
 C  L  T  Q  L  N  A  K  D  I  T  D  D  D  K  Q  E  L  D  E     180

GCTCTGCAGAGAGAGATCCAAGCAGCCTTCAGAACTGATGAAATCAGGAGGGCACAACCC    602
 A  L  Q  R  E  I  Q  A  A  F  R  T  D  E  I  R  R  A  Q  P     200

ACCCCACAGGACGAAATGCGCTATGGGATGAGCTACATCCATGAGACTGTATGGAAGGGC    662
 T  P  Q  D  E  M  R  Y  G  M  S  Y  I  H  E  T  V  W  K  G     220

GTGCCTAAGTTCTTGCGCCGTGTGGATACAGCCCTGAAGAATATCGGCATCAATGAGCGC    722
 V  P  K  F  L  R  R  V  D  T  A  L  K  N  I  G  I  N  E  R     240
```

Fig. 1-3

```
CTTCCCTACAATGTTTCTCTCATTCGGTTCTCTTCTTGGATGGGTGGTGACCGCGATGGA    782
 L  P  Y  N  V  S  L  I  R  F  S  S  W  M  G  G  D  R  D  G     260

AATCCAAGAGTTACCCCGGAGGTGACAAGAGATGTATGCTTGCTGGCCAGAATGATGGCT    842
 N  P  R  V  T  P  E  V  T  R  D  V  C  L  L  A  R  M  M  A     280

GCAAACTTGTACATCGATCAGATTGAAGAGCTGATGTTTGAGCTCTCTATGTGGCGCTGC    902
 A  N  L  Y  I  D  Q  I  E  E  L  M  F  E  L  S  M  W  R  C     300

AACGATGACGTTCGCGTTCGTGCCGAAGAGCTCCACAGTTCGTCTGGTTCCAAAGTTACC    962
 N  D  D  V  R  V  R  A  E  E  L  H  S  S  S  G  S  K  V  T     320

AAGTATTACATAGAATTCTGGAAGCAAATTCCTCCAAACGAGCCCTACCGGGTGATACTA   1022
 K  Y  Y  I  E  F  W  K  Q  I  P  P  N  E  P  Y  R  V  I  L     340

GGCCATGTAAGGGACAAGCTGTACAACACACGGAGCGTGCTCGCCATCTGCTGGCATCT   1082
 G  H  V  R  D  K  L  Y  N  T  R  E  R  A  R  H  L  L  A  S     360

GGAGTTTCTGAAATTTCAGCGGAATCGTCATTACCAGTATCGAAGAGTTCCTTGAGCCA   1142
 G  V  S  E  I  S  A  E  S  S  F  T  S  I  E  E  F  L  E  P     380
```

Fig. 1-4

```
CTTGAGCTGTGCTACAAATCACTGTGTGACTGCGGGAGACAAGGCCATCGCGGACGGGAGC   1202
 L  E  L  C  Y  K  S  L  C  D  C  G  D  K  A  I  A  D  G  S     400

CTCCTGGACCTCCTGCGCCAGGTGTTCACGTTCGGGCTCTCCCTGGTGAAGCTGGACATC   1262
 L  L  D  L  L  R  Q  V  F  T  F  G  L  S  L  V  K  L  D  I     420

CGGCAGGAGTCGGAGCGGCACACCGACGTGATCGACGCCATCACCACGCACCTCGGCATC   1322
 R  Q  E  S  E  R  H  T  D  V  I  D  A  I  T  T  H  L  G  I     440

GGGTCGTACCGCGAGTGGTCCGAGGACAAGAGGCAGGAGTGGCTGCTGTCGGAGCTGCGA   1382
 G  S  Y  R  E  W  S  E  D  K  R  Q  E  W  L  L  S  E  L  R     460

GGCAAGCGCCCGCTGCCCCCGGACCTTCCCCAGACCGACGAGATCGCCGACGTCATC     1442
 G  K  R  P  L  P  P  D  L  P  Q  T  D  E  I  A  D  V  I       480

GGCGCGTTCCACGTCCTCGCGGAGCTCCCGGACAGCTTCGGCCCCTACATCATCTCC     1502
 G  A  F  H  V  L  A  E  L  P  P  D  S  F  G  P  Y  I  I  S    500

ATGGCGACGGCCCCCTCGGACGTGCTCGCCGTAGAGCTCCTGCAGCGCGAGTGCGGGGTG   1562
 M  A  T  A  P  S  D  V  L  A  V  E  L  L  Q  R  E  C  G  V    520
```

Fig. 1-5

```
CGGCCAGCCGTGCCCGTGGTGCCGCTGTTCGAGAGGCTGGCCAGCCTGCAGCTGCGCCCG    1622
 R  P  A  V  P  V  V  P  L  F  E  R  L  A  S  L  Q  L  R  P    540

GCGTCCGTGGAGCGGCGCCTCTTCTCGGTGGACTGGTACATGGACCGGATCAAGGGCAAGCAG  1682
 A  S  V  E  R  L  F  S  V  D  W  Y  M  D  R  I  K  G  K  Q    560

CAGGTCATGGTCGGCTACTCCGACTCCGGCAAGGACGCCGGCCGCCTGTCCGGGGCGTGG    1742
 Q  V  M  V  G  Y  S  D  S  G  K  D  A  G  R  L  S  A  A  W    580

CAGCTGTACAGGGCGCAGGAGGAGATGGCGCAGGTGGCCAAGCGCTACGGGGTCAAGCTC    1802
 Q  L  Y  R  A  Q  E  E  M  A  Q  V  A  K  R  Y  G  V  K  L    600

ACCTTGTTCCACGGCCGCGGAGGCGGTGGGCAGGGGCCCACGCACCTTGCC    1862
 T  L  F  H  G  R  G  G  T  V  G  R  G  G  G  P  T  H  L  A    620

ATCCTGTCCCAGCCGCCGGACACCATCAACGGGTCCATCCGTGTGACGGTGCAGGGCGAG    1922
 I  L  S  Q  P  P  D  T  I  N  G  S  I  R  V  T  V  Q  G  E    640

GTCATCGAGTTCTGCTTCGGGGAGGAGCACCTGTCGTTCCAGACTCTGCAGCGCTTCACG    1982
 V  I  E  F  C  F  G  E  E  H  L  S  F  Q  T  L  Q  R  F  T    660
```

Fig.1-6

```
GCCGCCACGCTGGAGCACGGCATGCACCCGGTCTCTCCCAAGCCCGAGTGGCGCAAG   2042
 A  A  T  L  E  H  G  M  H  P  P  V  S  P  K  P  E  W  R  K    680

CTCATGGACGAGATGGCGGTCGTGGCCACGGAGGAGTACCGCTCGGTCGTCGTCAAGGAG   2102
 L  M  D  E  M  A  V  V  A  T  E  E  Y  R  S  V  V  V  K  E    700

CCGCGCTTCGTCGAGTACTTCAGATCGGCTACACCGGAGACCGAGTACGGGAGGATGAAC   2162
 P  R  F  V  E  Y  F  R  S  A  T  P  E  T  E  Y  G  R  M  N    720

ATCGGCAGCCGGCCAGCCAAGAGAAGGAGGCCCGGCCATCACGACCCTGCGCGCCATC   2222
 I  G  S  R  P  A  K  R  R  R  P  G  G  G  I  T  T  L  R  A  I  740

CCCTGGATCTTCTCGTGGACTCAGACCCGATTCCACCTTCCCGTGTGGCTGGGAGTCGGC   2282
 P  W  I  F  S  W  T  Q  T  R  F  H  L  P  V  W  L  G  V  G    760

GCCGCCTTCAAGTTCGCCATCGACAAGGACGTCAGGAACTTCCAGGTCCTCAAAGAGATG   2342
 A  A  F  K  F  A  I  D  K  D  V  R  N  F  Q  V  L  K  E  M    780

TACAACGAGTGGCCATTCTTCAGGGTCACCCTGCTGGACCTGCTGGAGATGGTTTTCGCCAAG   2402
 Y  N  E  W  P  F  F  R  V  T  L  D  L  L  E  M  V  F  A  K    800
```

Fig. 1-7

```
GGAGACCCCGGCATTGCCGGCTTGTATGACGAGCTGCTTGTGGCGGAAGAACTCAAGCCC    2462
 G  D  P  G  I  A  G  L  Y  D  E  L  L  V  A  E  E  L  K  P      820

TTTGGGAAGCAGCTCAGGGACAAATACGTGGAGACACAGCAGCTTCTCCTCCAGATCGCT    2522
 F  G  K  Q  L  R  D  K  Y  V  E  T  Q  Q  L  L  L  Q  I  A      840

GGGCACAAGGATATTCTTGAAGGCGATCCATTCCTGAAGCAGGGCTGGTGCTGCGCAAC     2582
 G  H  K  D  I  L  E  G  D  P  F  L  K  Q  G  L  V  L  R  N      860

CCCTACATCACCACCCTGAACGTGTTCCAGGCCTACACGCTGAAGCTGAAGCGCATCCGCGACCCC   2642
 P  Y  I  T  T  L  N  V  F  Q  A  Y  T  L  K  R  I  R  D  P      880

AACTTCAAGGTGACGCCCCAGCCCCCGCTGTCCAAGGAGTTCGCCGACGAGAACAAGCCC    2702
 N  F  K  V  T  P  Q  P  P  L  S  K  E  F  A  D  E  N  K  P      900

GCCGGACTGGTCAAGCTGAACCCGGCGAGCGAGTACCCGCCCGGCCTGGAAGACACGCTC    2762
 A  G  L  V  K  L  N  P  A  S  E  Y  P  P  G  L  E  D  T  L      920
```

Fig.1-8

```
ATCCTCACCATGAAGGGCATCCCGGCCGGGCATGCAGAACACTGGCTAGGCGGGCTTCTCTT  2822
 I  L  T  M  K  G  I  R  A  G  M  Q  N  T  G
CACTCACCTGCAGAGTGCACCGGCAATAATCAGCTTCCGGATGGTGGCCGTTTTGTCAGTT  2882
                                                                 7
TTGGATGGAAATGCCGAACTGGCCAGCGTCTGTTTTCCCTATGCATATGTAATTTCCTGC  2942
                                                                27
CTCTTTATATTCACTCTTGTTGTCAAGTCCAAGTGGAAAATCTTGGCATATTATACATAT  3002
                                                                47
TGTAATAATAAGCATCGTACAATCTGCAAAAAAAAAAAAAAAAAAAAAAAAAAA  3059
                                                          66
```

GENE FOR CORN PHOSPHOENOLPYRUVATE CARBOXYLASE

The present invention relates to a DNA sequence coding for corn phosphoenolpyruvate carboxylase [E.C.4.1.1.31] and a plasmid carrying such DNA sequence. Phosphoenolpyruvate carboxylase (PEPCase) is an enzyme which plays an important role in photosynthetic carbon dioxide fixation in corn (or maize in England).

PEPCase is naturally found in all of the higher plants, algae, most protists, and various bacteria, and irreversibly catalyzes the photosynthetic reaction in which carbon dioxide is fixed to phosphoenolpyruvic acid to form oxaloacetic acid (OAA) and phosphoric acid as shown in the following schema:

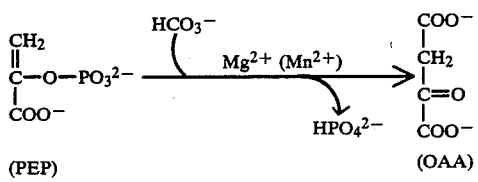

Biochemical properties of PEPCase, such as the sedimentation constant, molecular weight, and the number of subunits, vary from species to species. As far as the corn PEPCase is concerned, electrophoretically homogenous preparation was obtained and the enzyme was reported to have a molecular weight of 400,000[1]. In addition, it is generally known that (A) the PEPCase derived from the corn is an allosteric enzyme[2], (B) when a faded corn leaf or greening corn leaf is exposed to an intense light, the activity of the enzyme contained therein is increased five times[3], and (C) the increased activity is attributable to the increase of mRNA level[4].

However, in regard to the gene coding for the corn PEPCase, there are only two reports. One of them teaches that the gene is supposed to be present in chloroplast DNA as well as in nuclei[5] and the other reports that a part (500 bp) of cDNA for the gene has been successfully cloned[6].

As previously stated, the corn PEPCase plays an important role in photosynthetic carbon dioxide fixation and, therefore, cloning of the gene encoding the enzyme and determination of the nucleotide sequence thereof are industrially very important. Thus, successful cloning of the PEPCase gene will enable modification of the gene and integration of the modified gene into a plant culture, which will, in turn, bring an increased fixation efficiency of carbon dioxide and, therefore, a good harvest of corn starch.

In view of the above facts, the applicant has made every effort to clone the gene coding for the corn PEPCase and succeeded in selecting a cDNA segment encoding a substantially functional part of the enzyme from a cDNA library which had been obtained by reverse transcription of mRNA, cloning the cDNA segment, and determining the nucleotide sequence thereof.

Accordingly, the present invention provides the DNA sequence encoding the substantially functional part of the corn PEPCase and a vector plasmid carrying such DNA sequence. The DNA sequence, or gene, will be referred to as corn ppc hereinafter.

The manner in which these and other objects are accomplished and advantages of the invention are obtained will become more apparent from the detailed description which follows and from the accompanying drawings in which:

FIG. 1 illustrates the DNA sequence of the corn ppc encoding the corn PEPCase and corresponding amino acid sequence;

Figure 2:
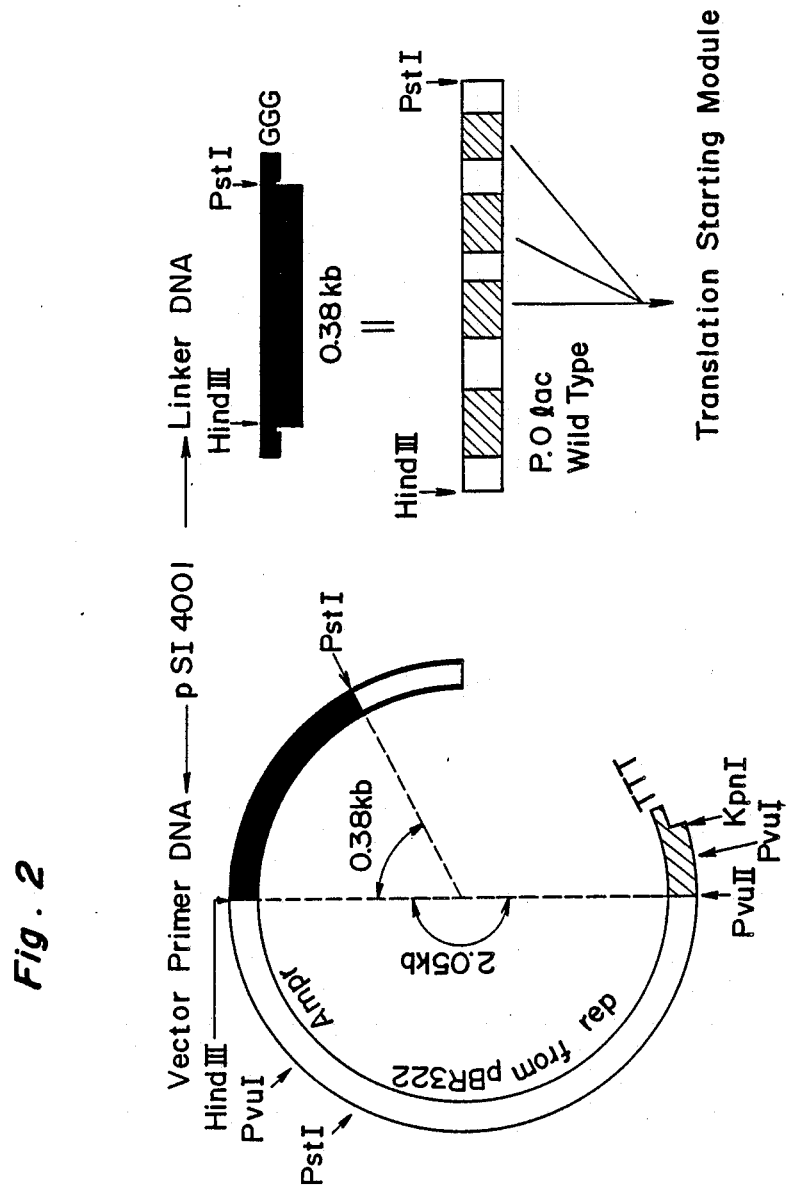
FIG. 2 illustrates the structure of the vector primer and linker DNA employed in the construction of a genetic library for corn cDNA.
Figure 3:
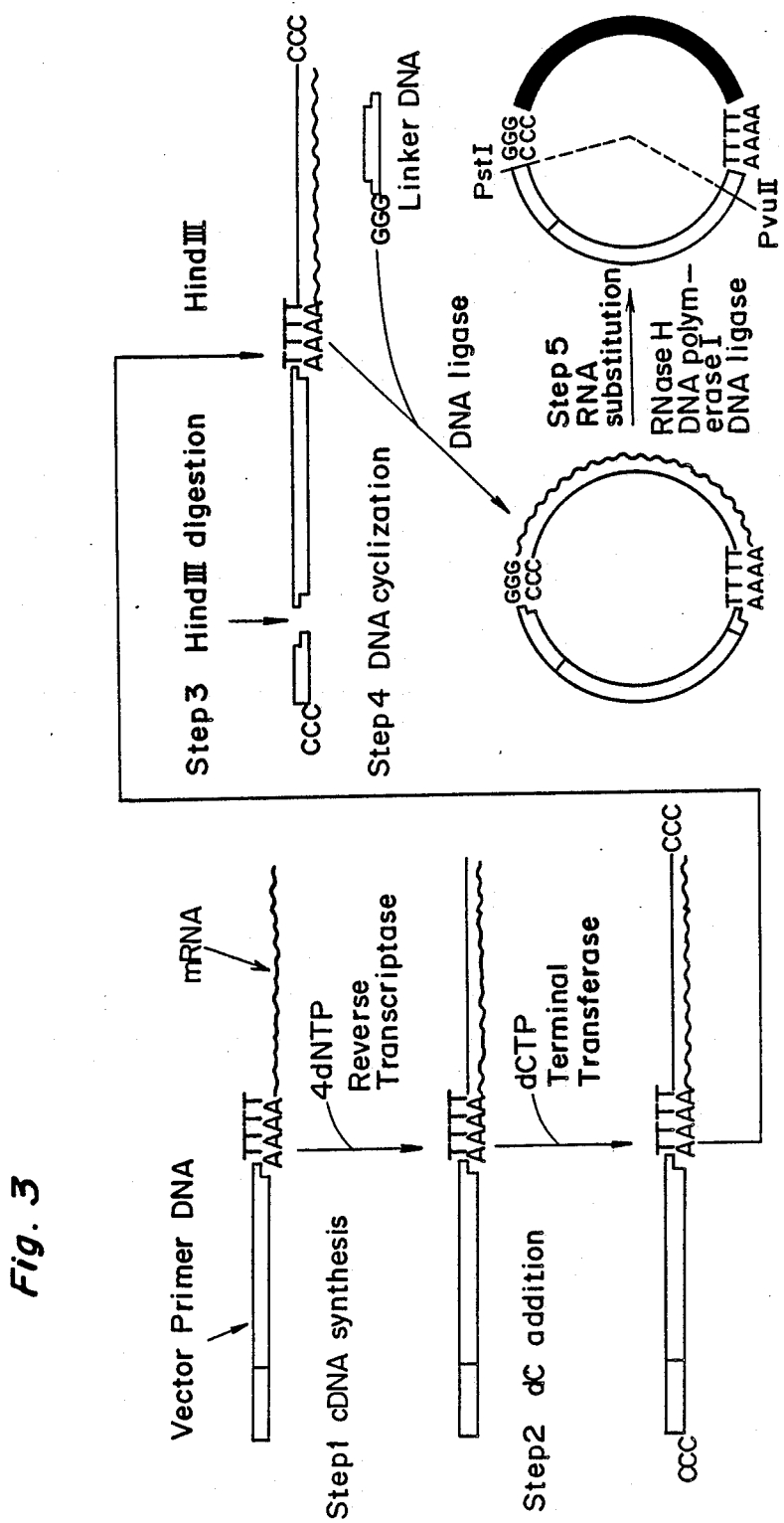
FIG. 3 is a diagram of Okayama-Berg method.

The term "DNA sequence encoding substantially functional part of the corn PEPCase" herein used means either the DNA sequence encoding the total amino acid sequence of the corn PEPCase, or a DNA sequence which contains such DNA sequence and an additional DNA sequence which does not adversely affect the transcription and translation of the DNA sequence, or the DNA sequence which encodes the minimum part of the total amino acid sequence which is necessary to exhibit the PEPCase activity, or a DNA sequence which consists of one of the above mentioned DNA sequences, regulatory gene(s) essential for the expression of the DNA sequences, and it associated genes. In other words, this term is functionally defined in a sense that the corn PEPCase activity can be expressed by the use of the DNA sequence and does not physico-chemically denote a single substance. A DNA sequence encoding the substantially functional part of the corn PEPCase is illustrated in FIG. 1 of the accompanying drawing.

Cloning of Corn ppc and Determination of the Base Sequence

A. Reagents Employed in Experiments

Restriction enzyme Eco RI was obtained from Nippon Gene Co. Ltd., and other restriction enzymes and λ-DNA used as a molecular marker were purchased from Takara Shuzo Co. Ltd. RNase A, RNase T1, lysozyme, dithiothreitol and bovine serum albumin (BSA) were from Sigma and ethidium bromide (EtdBr) was from Aldrich Chemical. [α-$^{32}$P]dCTP was obtained from Amersham Co. Ltd. Dotite agarose was used for electrophoresis.

B. Materials Employed in Experiments

*Esherichia coli* K-12 variants PCR1[7] and DH1 were used in the present invention. The former was constructed by the inventor and the latter was presented from Virus Research Institute, Kyoto University. The strain K-12 PCR1 was deposited at the Fermentation Research Institute, Japan, under the assession number FERM P-7783 and DH1 strain is publicly available from the above-mentioned institute, Kyoto University. The genotype and phenotype of the strains PCR1 and DH1 are F−, recA, rpsL(Str$^r$), thi, arg, thr, leu, ppc−(Glu−) and F−, recA 1, endA 1, gyrA 96, thi 1, hsdR 17 (r−$_k$, m+$_k$), supE 44, respectively. Vector plasmid pSI4001 employed in the present invention is publicly available from the afore-mentioned institute of Kyoto University. Corn seeds were those of mating type presented by Crop Science Section, Agricultural Department, Kyoto University.

C. Culture of *E. coli* Strain and Corn Plant

1. Culture of *E. coli* Strain

The composition of the culture medium employed in the cultivation of *E. coli* strain is shown in Table 1. An eutrophic medium, LB medium, was used for routine cultivation. A selection medium for auxotrophy was prepared on the basis of a minimum medium, E-medium. Thus, Glu⁻ medium was so prepared that it contains required amino acids for *E. coli* PCR1 and glucose as a sole carbon source, while Glu⁺ medium was prepared by adding glutamic acid to the Glu⁻ medium. A solid medium was prepared by the addition of 1.5% (w/v) of agar to a liquid medium. As a selection pressure, 25 μg/ml of streptomycin (Str), 50 μg/ml of ampicillin (where eutrophic medium is employed), or 25 μg/ml of ampicillin (where other medium is employed) was supplemented to a medium as necessary. When autoclave sterilization is required, the medium components were separated as shown in Table 1 and separately sterilized. An antibiotic was added to the sterilized medium at below 55° C. A liquid cultivation was conducted using TAIYO Incubator M-100$^N$ with shaking and a solid cultivation was conducted in an incubator at 32° C.

TABLE 1

Culture medium employed in cultivation of *E. coli*

| LB-medium (in 1 liter) | |
|---|---|
| bacto yeast extract | 5 g |
| bacto tryptone | 10 g |
| NaCl | 5 g |
| glucose | 1 g |
| 1N NaOH | 8 ml |
| (agar) | |

Glu⁻ medium

Following substances are added to E-medium* for preparing Glu⁻ medium. (final concentration)

| | |
|---|---|
| L-leucine | 100 μg/ml |
| L-arginine | 100 μg/ml |
| L-threonine | 100 μg/ml |
| thiamin | 3 μg/ml |
| **CRM solution | 1 ml |
| glucose | 0.5% |
| (agar) | |

Glu⁺ medium

One mg/ml of glutamic acid is added to the Glu⁻ medium (adjusted to pH 7.2)

*E-medium (50-fold concentration)

| | |
|---|---|
| water | 670 ml |
| MgSO₄.7H₂O | 10 g |
| citric acid hydrate | 100 g |
| K₂HPO₄ | 500 g |
| NaNH₄HPO₄.4H₂O | 175 g |

After dilution, 7 ml of NaOH is added per 1 liter of the medium.

**CRM solution (in 1 liter)

| | |
|---|---|
| FeCl₃.6H₂O | 480 mg |
| MnCl₂.4H₂O | 280 mg |
| CaCl₂ | 270 mg |
| ZnCl₂ | 2000 mg |
| H₃BO₃ | 290 mg |
| CoBO₄ | 130 mg |

Note 1: All of the compoments of LB-medium are dissolved in water together and autoclave-sterilized, while glucose and/or agar are added after sterilization in the case of Glu⁻ medium.
Note 2: Agar is added when a solid medium is desired.

*E. Coli* strain was grown on LB-medium. When the culture reached the stationary phase, it was stored at −20° C. after addition of glycerol to a concentration of 50%.

2. Culture of Corn

Corn seeds which had been immersed in running water overnight were planted on a wetted sanitary cotton placed in a container of an appropriate size. The seeds were germinated in an air-conditioned room at 28° C. Ten days after germination, the leaves were greened by exposure to light for three days. The greened leaves were employed for the preparation of mRNA.

D. General Procedure on Experiments

1. Abbreviation

The abbreviation for reagents used in the experiments are as follows:
20×SSC: NaCl (175 g) and sodium citrate.2H₂O (88 g) in 1 liter
TE: 1 mM EDTA and 10 mM Tris-HCl buffer, pH 8.0
TAE: 2 mM EDTA, 40 mM Tris and 20 mM acetate buffer, pH 8.05

2. Assay of DNA and RNA

Any of the following three measures was employed in the quantitative analysis of DNA and RNA.

(i) Spectrophotometric Determination

Absorbance of DNA or RNA at 260 nm ($A_{260}$) was measured using a spectrophotometer. Calculation was made on the basis of the absorbance of 20 and 23 in terms of 1 mg DNA and RNA /ml solution, respectively. This method was applied to partially purified preparation for the purpose of obtaining comparatively exact value.

(ii) Fluorometric Determination

This method is based on the reaction between m-diaminobenzoic acid 2HCl and deoxyribose which has been liberated from DNA by the action of perchloric acid. Thus, a quinaldine analogue exhibiting an intense fluorescence, which yields according to the following schema, is fluorometrically measured in this method[8]. This method is employed in the precise determination of a trace amount of DNA.

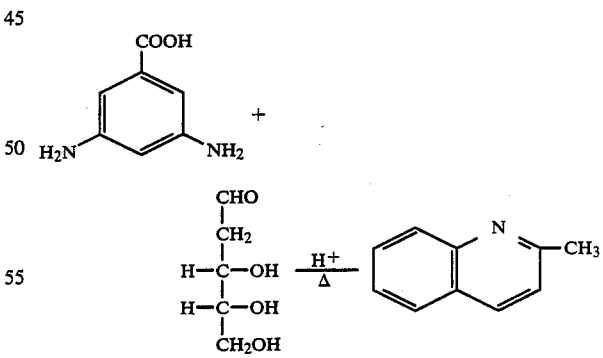

The fluorometric determination was conducted with an excitation wave length of 406 nm and emission wave length of 520 nm, using a Hitachi Fluorophotometer Type 204.

The concentration of a standard DNA sample (λ-DNA and salmon sperm DNA) was measured at 260 nm. A dilution series of the standard DNA sample was prepared and the calibration curve was constructed using the same.

The sample to be tested is first added with perchloric acid to the final concentration of 0.5 M and incubated at 70° C. for 20 minutes. The same volume of a reagent mixture which has been prepared by incubating at 37° C. for one hour a mixture of 10 mM $Na_2CO_3$ dissolved in 1 M NaOH and diaminobenzoic acid 2HCl (3 vol/1 vol) is then added to start the reaction. After one hour incubation at 70° C., 6.25 volumes of 1 M HCl is added. The reaction is terminated by ice-cooling, and fluorescence is measured.

(iii) Spot Test

This test was employed to determine DNA- or RNA-containing fractions after column chromatography. In general, 7.5 μl portion of the fraction to be tested is combined with 2.5 μl of EtdBr (2 μg/ml) and the mixture is spotted on Saran film spreaded on a Petri dish. The spot is observed with a short wave uv illuminometer and photographed. The concentration of DNA or RNA in the fraction is determined by comparing its fluorometric intensity with that of the standard.

EXAMPLE

A. Preparation of Corn Poly A+ RNA[4), 9),10)]

Poly A+ RNA was prepared for the purpose of cloning cDNA containing corn ppc. Throughout the entire process which includes the preparation of the RNA sample and the cloning of cDNA, contamination by RNase should be avoided with care. Accordingly, containers, pipettes, distilled water, buffers, etc. were all sterilized before use, and all the manipulations were carried out using gloves.

Corn seeds were germinated in the dark and ten day old seedlings were light-induced for three days. The resultant leaves (3.8 g) were frozen in liquid nitrogen and powdered using a mortar and pestle which have previously been cooled to −20° C. The resulting powder was mixed with a buffer solution for extraction, and the mixture was homogenized. The buffer solution employed above was prepared by combining a mixture of a reagent grade of guanidine thiocyanate (50 g)(Fluka Co. Ltd.), sodium N-lauroylsarcosinate (0.5 g), 1 M sodium citrate (pH 7.0)(25 ml), and 2-mercaptoethanol with deionized water to make 100 ml, adjusting the pH of the resultant aqueous mixture to 7.0, and passing the mixture through Millipore Filter. The guanidine thiocyanate and sodium N-lauroylsarcosinate are intense protein-denaturing agents, in the presence of which RNase is inactivated.

The homogenate obtained above was transferred to a 30 ml COREX tube and centrifuged at 10° C. for 10 minutes by the use of Beckman J-21B centrifuge (13,000 rpm). The supernatant was recovered and centrifuged again. To the recovered supernatant was added CsCl and $Na_2$ EDTA to concentrations 5.7 M and 0.1 M, respectively (1.2 ml, pH 7.0) in a polyallomer tube. The tube was centrifuged at 25° C. for 12 hours in a Hitachi 65P Ultra-centrifuge (35,000 rpm). The supernatant rich in RNase was carefully removed using an aspirator so that the aspirator might not contact RNA precipitated in the form of a transparent gel. The RNA was washed several times with 99.5% ethanol to remove CsCl, lyophilized, and dissolved in 0.2 M NaCl solution. To the solution is added 2.5 volumes of 95% ethanol at −20° C. and the mixture was left stand overnight and ethanol-precipitated. RNA thus obtained, which was designated as "total RNA" (1,800 μg), was dissolved in sterilized water (0.5 ml).

2. Selection of Poly A+ RNA by Oligo(dT)cellulose Column Chromatography

Poly A+ RNA is selectively adsorbed to oligo(dT)cellulose via hydrogen bond formation when the total RNA dissolved in an NaCl solution of high concentration (i.e. adsorption buffer) is passed through the column packed with the oligo(dT) cellulose. After adsorption, the column is washed with a NaCl solution of lower concentration (i.e., elution buffer), whereby the hydrogen bond is cleaved and the poly A+ RNA is recovered.

Oligo(dT)cellulose Type 7 (Pharmacia P-L Biochemicals) was packed in a column (inner diameter 0.5–0.8 cm, bed volume 0.5 ml) and washed with 3 volumes of sterilized water, 0.1 M NaOH-5 mM EDTA, and sterilized water until the washings showed pH below 8. The column was then equilibrated with TE adsorption buffer(pH 7.5, 0.5 M NaCl) and washed with 5 volumes of fresh adsorption buffer. The total RNA was then loaded on the column, which had been heated at 65° C. for 5 minutes, diluted with 2 volumes of adsorption buffer and cooled rapidly on ice. Such RNA treatment was done for denaturating the RNA which generally takes a random coil form due to intramolecular hydrogen bonds, and accordingly for efficient formation of the hydrogen bond between the poly A+ portion of the RNA and the oligo(dT) moiety of cellulose. The eluate was loaded again on the column and each 30 drops of second eluate was collected in an Eppendorf tube. The flow rate was 0.31 ml/min. After the elution with the adsorption buffer(10 ml), the column was run with TE eluting buffer (pH 7.5) at a flow rate of 0.16 ml/min. and each 10 drops (ca.0.4 ml) of the eluent was collected in an Eppendorf tube. Fractions containing poly A+ RNA were detected by the spot test and a total of 1.2 ml of fractions were collected. To the collected solution were added 4 M NaCl (63 μl) and then 2.5 volumes of 95% ethanol at −20° C. The ethanol-precipitated solution was kept at −70° C. overnight. The precipitate was dissolved in water, and the optical density ($A_{260}$) of the aqueous solution was measured, which revealed the absence of RNA. Accordingly, sodium acetate was added to the mother liquor of the ethanol-precipitation procedure to a final concentration of 0.1 M (pH 5.2). To the mixture was added ethanol, and the resultant precipitate was measured in the same manner as described above to show the presence of 3.51 μg of RNA (234 μg/ml). $A_{260}/A_{280}$ was 2.75. Poly A+ RNA thus obtained was dissolved in a TE buffer, added with 2.5 volumes of 95% ethanol, stored at −70° C., and used for a subsequent cDNA cloning procedure.

B. Cloning and Sequencing of cDNA Derived from Poly A+ RNA Otained Above

1. Construction of a Genetic Library of Corn cDNA

A cDNA library for corn's PEPCase was constructed using the poly A+ RNA obtained above.

The known procedure for cloning cDNA consists of the following steps: constructing a double stranded DNA carrying a hair-pin structure at one end, through a self-priming reaction, by starting from a cDNA which was synthesized in vitro by reverse transcription of mRNA; excising the hair-pin structure by S1 nuclease; and integrating the resultant double stranded DNA into a vector after the addition of a homopolymer or linker having appropriate restriction sites. This procedure has drawbacks in that 5'-terminal sequence of mRNA is not reflected in the resultant double stranded DNA, and that the yield of the DNA is insufficient and a long cDNA in length is difficult to obtain due to material and manipulative limitations, and that a partial secondary structure is liable to generate during the synthetic process of the second DNA strand because the template DNA is a single strand, and, such secondary structure often inhibits DNA polymerase I from synthesizing the second DNA strand. Accordingly, Okayama-Berg method[9),10),11)] which has overcome the above drawbacks to a great extent was employed in the cloning process of the corn cDNA.

According to Okayama-Berg method, a vector primer is constructed by attaching dT chain to one end of a given vector which has been linearized, and used as a primer for synthesis of a first cDNA single strand in the presence of poly A+ mRNA. The vector-primer used in the present invention is presented in FIG. 2 of the accompanying drawing. After completion of the synthesis of the first cDNA single strand, a 3'-terminal of the first strand is linked with the other end of the vector-primer to recover a ring form, while maintaining mRNA as it is. The vector is then repaired by treating with RNase H, polymerase I and DNA ligase, whereby mRNA is eliminated and a double stranded DNA generates within the vector.

The above procedure lacks self-priming and S1 nuclease digestion steps and, therefore, prevents the loss of 5'-terminal sequence mentioned above. In addition, the undesired formation of the secondary structure is minimized in this improved procedure because the double stranded DNA is established via the repair reaction on mRNA:cDNA hybrid. An additional advantage of the procedure resides in that a series of reactions can sequentially be carried out in microcentrifuge tubes and do not include a selecting process of products by size, which is troublesome and often causes loss of the products. Accordingly, the improved process permits a rapid cloning of the desired gene fragment with a high yield.

STEP 1. Preparation of cDNA

A poly A+ RNA solution (15 μl, 234 μg/ml) was subjected to a denaturing treatment by heat and then vacuum dried. Distilled water (16 μl) and methylmercuric hydroxide (1 μl) were added thereto and the mixture was allowed to stand at room temperature for 10 minutes. The mixture was
then added with 0.7 M β-mercaptoethanol (3 μl) and left to stand for 5 minutes. To the mixture was added at 37° C. a reaction mix (40 μl) which comprised 50 mM Tris-HCl buffer, pH 8.3, 8 mM MgCl$_2$, 30 mM KCl, 3 mM dithiothreitol, 2 mM dATP, dTTP, dGTP, dCTP, 0.25 μCi/nmol [α-$^{32}$P]*dCTP, and vector-primer DNA (1 μg), and the resulting solution was pre-incubated at 37° C. for 5 minutes. After incubation, 12.9 units/μl of reverse transcriptase (5 μl) (Seikagaku Kogyo, Japan) was added to the solution and allowed to react at 37° C. for 60 minutes. The synthetic reaction of cDNA was monitored by sampling 1 μl of the reaction mixture at 0, 30 and 60 minutes after initiation of the reaction and followed by measuring the incorporation of $^{32}$P into the resulting TCA precipitate. The reaction was terminated by the addition of 0.25 M EDTA (4.5 μl) and 10% SDS (4.5 μl), and the mixture was extracted with phenol and chloroform (60 μl). The remaining aqueous layer was mixed with 4 M ammonium acetate (60 μl) and 95% ethanol (240 μl), frozen at −70° C. for 15 minutes, and centrifuged at 15,000 rpm for ten minutes. The resultant precipitate was dissolved in TE buffer (30 μl), pH 7.3, and subjected to the standard ethanol precipitation after addition of 4 M ammonium acetate (30 μl) and 95% ethanol (120 μl).

STEP 2. Addition of dC chain

The precipitate obtained above was dissolved in a reaction mix comprising 140 mM sodium cacodylate, 30 mM Tris-HCl buffer, pH 6.8, 1 mM CoCl$_2$, 0.1 mM dithiothreitol, 0.66 μg poly A, and 330 μM [α-$^{32}$P]dCTP (10 μCi), and the mixture was incubated at 37° C. for 2 to 3 minutes. After the addition of 54 units of terminal transferase (Life Science), the mixture was incubated for 5 minutes and rapidly cooled to 0° C. in order to temporarily stop the reaction. After sampling (1 μl) from the mixture, $^{32}$P incorporation was measured by TCA precipitation, and the length of dC chain attached to the cDNA was estimated to be 20 base pairs on the average. Since the favorable chain length of dC is known to be 10 to 20 base pairs, the reaction was terminated by addition of a mixture (6.75 μl) of 0.25 M EDTA and 10% SDS (1:1, v/v). On the reaction mixture, phenol and chloroform (45 μl) extraction, ethanol precipitation (×2) and ethanol washing were conducted in the same manner as in step 1.

STEP 3. Hind III digestion

The precipitate obtained above was dissolved in a Hind III buffer (30 μl). The solution was added with 5 units of Hind III (NEB) and kept at 37° C. for 60 minutes to allow digestion. The reaction was stopped by adding the afore-mentioned EDTA SDS mixture (3 μl), extracted with phenol and chloroform (30 μl), ethanol precipitated (×2), and washed with ethanol. The resultant precipitate was dissolved in TE buffer (15 μl), pH 7.3, and stored at −20° C. after addition of ethanol (15 μl).

STEP 4. Cyclization of vector by means of linker DNA carrying dG chain

For cyclization, there were employed the above-obtained vector carrying cDNA:mRNA at a concentration of 0.03 pmol/μl and a linker DNA at a concentration of 0.10 pmol/ml. The vector and the linker were mixed at a ratio of 1.0 μl:0.2 μl (No.1), 1.0 μl:0.4 μl (No.2-A, B, C), and 1.0 μl:0.6 μl (No.3), and the resultant mixtures were treated as described below.

The formation of G-C hydrogen bond, cyclization and ligation were sequentially performed as follows.

The above mixture comprising the vector and the linker was combined with a mixture (10 μl) of TE buffer, pH 7.5, plus 0.1 M NaCl, incubated at 65° C. for 5 minutes and then at 42° C. for 30 minutes (annealing), and finally cooled to 0° C. To the resultant solution were added E. coli DNA ligase (NEB) and a cyclization buffer (90 μl) comprising 1 mM DTT, 20 mM Tris-HCl buffer, pH 7.5, 4 mM MgCl$_2$, 10 mM (NH$_4$)$_2$SO$_4$, 0.1 M KCl, 0.1 mM β-NAD (nicotinamide adenin dinucleotide), and 50 μg/ml BSA, and the reaction mixture was incubated at 12° C. overnight. The amount of DNA ligase used was 2 units for samples No.1, No.2-B, No.3, 0.5 unit for No.2-A, and 10 units for No.2-C.

STEP 5. Substitution of RNA chain with DNA chain

To the reaction mixture obtained above were added a substrate mixture (4 μl) comprising 1 mM dATP, dTTP, dGTP, dCTP and 1.25 mM β-AND, E. coli DNA ligase, E. coli DNA polymerase I (Pharmacia PL Biochemicals), and E. coli RNase H (do.), and the reaction mixture was incubated at 12° C. for 60 minutes and then at 25° C. for 60 minutes, frozen at −20° C. and stored. The amount of each of the enzymes used above was shown below.

|  | DNA ligase | DNA polymerase | RNase H |
|---|---|---|---|
| No. 1, No. 2—B, No. 3 | 0.6 U | 2.8 U | 0.2 U |
| No. 2—A | 0.2 U | 0.7 U | ≦ 0.1 U |
| No. 2—C | 3 U | 14 U | 1.0 U |

STEP 6. Transformation of E. coli strain DH1

Competent E. coli DH1 cells frozen at −70° C. were thawed, and each 200 μl of the cell suspension was transferred into a microcentrifuge tube and left to stand at 0° C. for 15 minutes. To the tube was added an appropriate amount of the vector DNA obtained above, and the mixture was heat shocked at 42° C. for 90 seconds and cooled on ice for 2 minutes. To each tube, there was added at room temperature a psi medium (800 μl) comprising 2% (w/v) bacto tryptone (Difco), 0.5% bacto yeast extract (do.), 10 mM NaCl, 2.5 mM KCl, 10 mM MgSO$_4$ and 10 mM MgCl$_2$, and adjusted to pH 7.6 with KOH. The mixture was incubated at 37° C. for 60 minutes under shaking. An aliquot of the resultant mixture was plated on L broth containing ampicillin (50 μg/ml). On the other hand, the remainder of the mixture was combined with 50 volumes of the broth, and the mixture was shake-cultured at 37° C. for 3 hours, added with ampicillin at the final concentration of 100 μg/ml, continued to culture overnight, and employed as a library of corn cDNA.

Experimental Results

Sampling was made at several steps of the above cDNA cloning procedure, and each sample was subjected to agarose gel electrophoresis, alkali agarose gel electrophoresis and autoradiography. The results of these assays are detailed below.

The precipitated DNA (1 μl) obtained in Step 3 and a starting vector primer DNA (0.7 μg) were separately digested with Hind III and agarose gel electrophoresed. Hind III-digested vector-primer showed two bands at about 2.6 kb and 0.35 kb. Although the DNA obtained in Step 3 showed the similar bands, a band corresponding to that at 2.6 kb had a tail extending to the starting point. This indicated that corn mRNAs with various sizes had been attached to the vector-primer. The sample showed various bands around about 5.6 kb and it was considered to be a promising preparation for obtaining an appropriate library because corn ppc was expected to be about 3 kb.

2. Screening of Corn ppc cDNA (a) Experimental Procedure

E coli strain DH1 carrying the plasmids in which corn cDNA had been cloned (the plasmid hereinafter will be referred to as pM) was subjected to the alkali treatment[14] to obtain a cDNA library. E. coli strain PCR1 which requires glutamic acid was transformed with the library in accordance with the Rubidium method[15],[16],[17] and the cells were screened for the ability of complementing the glutamic acid requirement. The plasmid preparation by the alkali treatment varied depending on purposes with respect to the frequency (once or twice) of the alkali treatment and the presence or absence of RNase A or RNase T$_1$ treatment.

Since pM's promotor for transcription of corn cDNA was lac promotor of a wild type E. coli, Glu$^-$ medium, on which PCR1 transformed with pM is to be screened, was supplemented with $2.5 \times 10^{-5}$ M of isopropyl β-D-thiogalactoside (IPTG) which is a lactose analogue capable of inducing lac operon. In addition, glucose was substituted by glycerol so as to avoid a possible catabolite repression. Furthermore, a prescribed amount of ampicillin was added to the medium for screening. The cells were cultured at 30° C. which appeared an optimum temperature for corn PEPCase. Plasmids which complemented Glu-requirement of PCR1 were digested with appropriate restriction enzymes and characterized by agarose gel electrophoresis of the resultant fragments.

(b) Experimental Results

E. coli strain DH1 which harboured the plasmid carrying corn cDNA was subjected to the alkali treatment (twice) to obtain 1.77 mg/ml of pM (3.5 mg) according to A$_{260}$ determination.

E. coli PCR1 (ppc$^-$) was transformed with pM via the Rubidium method. About 8,400 colonies of transformants which acquired an ampicillin resistance were replica plated on Glu$^-$ plates, from which one colony was grown. This showed that the cells of the colony contained the plasmid which complemented the Glu-requirement of PCR1. This plasmid was designated pM5.

Based on the above finding, PCR1/pM5 was alkali treated to obtain 138 μg of plasmid DNA (pM5). Fresh PCR1 strain was transformed with the pM5. Transformants which acquired ampicillin resistance were all grown on Glu$^-$ medium, from which pM5's ability to complement Glu-requirement of PCR1 was confirmed. The plasmid pM5 was also treated with Pvu I to provide 1.82 kb DNA fragment unique to the starting cDNA cloning vector, which confirmed that pM5 was derived from the cloning vector.

Figure 4:
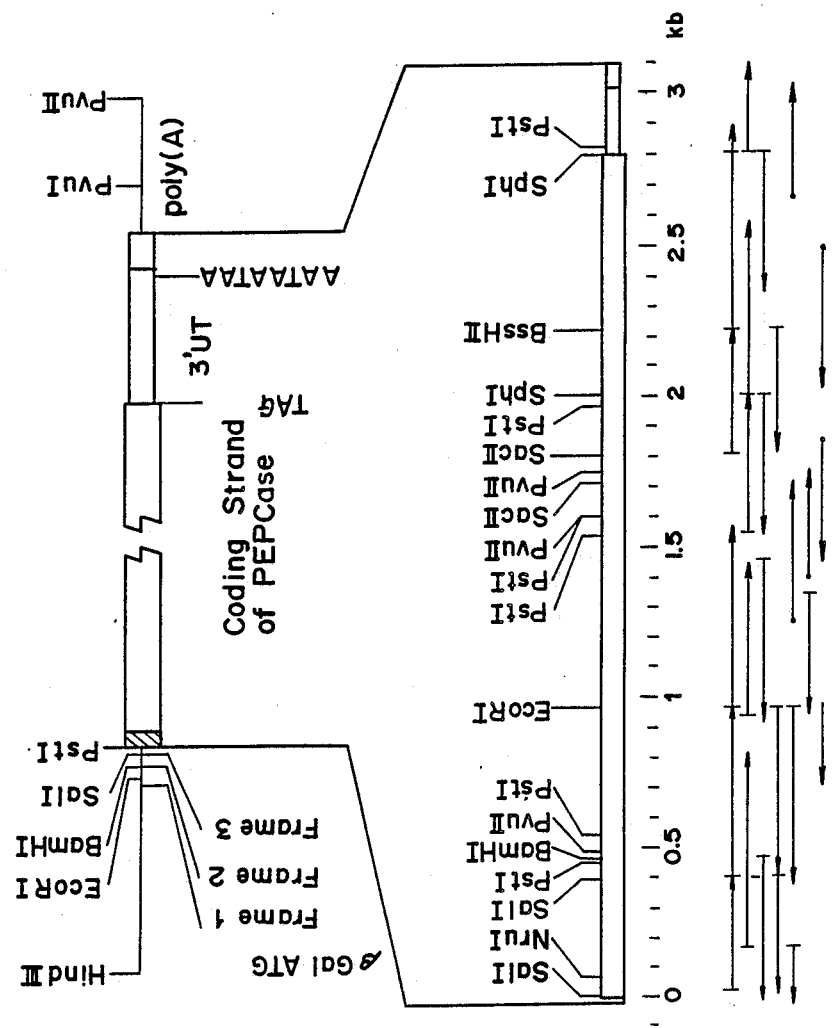
FIG. 4 is a restriction site map of plasmid pM52 which carries corn ppc.

The plasmid pM5 was about 6.30 kb and the integrated DNA was 3.40 kb, which appeared large enough to contain full-length ppc cDNA. The transformant PCR1/pM5 was subsequently grown to give a single colony, from which a plasmid renamed as pM52 (106 μg) was prepared. The resulting plasmid pM52 was digested with 13 restriction enzymes (6 cutters) and agarose gel electrophoresed. A restriction site map of pM52 is presented in FIG. 4 of the accompanying drawing. The bacteria transformed with plasmid pM52, i.e., E. coli K-12 PCR1/pM52 was deposited at the Fermentation Research Institute, Japan, under accession No. FERM p-8413 on Aug. 14, 1985.

The ppc gene inserted in pM52 was cleaved out of the plasmid, and DNA sequence thereof was determined by the sequencing strategy developed by F. Sanger[18] and improved J. Messing[19]. The DNA sequence determined and corresponding amino acid sequence are shown in FIG. 1.

(C) Study on Cell-Free Extract Containing
Recombinant Plasmid

1. Determination of PEPCase Activity and Effector Sensibitity on Cell-Free Extract (i) Experiment Cell-free extract of E. coli strain PCR1, Glu-requirement of which was complemented by transformation with pM plasmid, was prepared and measured on PEPCase activity. The PEPCase activity was determined by a coupled spectrophotometric method; the rate of decrease of absorbance of the reaction mixture at 340 nm associated with NADH oxidation in the presence of malic dehydrogenase (MDH, EC 1.1.1.37)[20] was followed. Modified Katagiri's method[21] was predominantly employed in this determination, in which 100 mM potassium phosphate buffer, pH 7.5, was used for cell suspension, and 20% glycerol and 1 mM dithiothreitol were added to the same buffer when the cells were ultrasonically disintegrated. The resultant suspension was centrifuged at $10^5 \times g$ for 1 hour to obtain the cell-free extract. Several substances regarded to be effective as an "effector" were added to the reaction mix, and their influences on the PEPCase activity were observed. Table 3 lists the composition of reaction mix employed in this test. Different from Katagiri's method, Tris-$H_2SO_4$ buffer, pH 8.0, was employed instead of Tris-HCl buffer, pH 8.0. Such substitution was necessary because $Cl^-$ ion inhibits E. coli PEPCase[22]. Quantitative analysis of proteins was conducted by the Lowry method[23].

TABLE 3

Composition of Reaction Mix for
Determination of PEPCase Activity

| |
|---|
| 100 mM Tris-$H_2SO_4$ buffer, pH 8.0 |
| 10 mM $KHCO_3$ |
| 10 mM $MgSO_4$ |
| 0.1 mM NADH |
| 1.51 U MDH |
| 2 mM PEP-CHA (phosphoenolpyruvic acid-cyclohexylammonium salt) |
| 10% (v/v) dioxane* |
| 10 mM aspartic acid* |
| 0.093 mM acetyl-CoA* |
| 10 mM glycine* |
| 10 mM malic acid* |
| 10 mM glucose 6-phosphate* |

Of above substances, those noted by an carrying asterisk were added when appropriate.

An additional investigation was made to examine the influence of three monoclonal antibodies[24] known to have an inhibitory action to E. coli PEPCase activity and of corn PEPCase antiserum[25] on PEPCase activity of the enzyme obtained by the method of the present invention.

(ii) Results

Table 4 below lists PEPCase activity and effector sensitivity of the cell-free extract of PCR1/pM52 as well as those of E. coli K-12 W3110, a wild type, used as a control. The upper and lower figures in each column show PEPCase activity in the absence and presence of an effector respectively. PEPCase activity is given in units/mg protein, and one unit is defined as the activity consuming 1 μmol of NADH per minute. The figures in parenthesis show the ratio (%) of activity when measured in the presence of an effector to that measured in the absence of the same.

TABLE 4

PEPCase Activity and Effector Sensitivity
of E. coli Cell Extract

| Effector | organism | |
|---|---|---|
| | PCR1/pM52 | W3110 |
| Dioxane | 0.052 | 0.004 |
| | 0.020(38) | 0.155(4304) |
| Aspartic Acid | 0.070 | 0.007 |
| | 0.065(94) | 0.000(0) |
| Acetyl CoA | 0.050 | 0.004 |
| | 0.056(112) | 0.117(3068) |
| Glycine | 0.056 | 0.005 |
| | 0.066(118) | 0.002(40) |
| Malic Acid | 0.062 | 0.003 |
| | 0.043(69) | 0.000(0) |
| Glucose-6-Phosphate | 0.051 | 0.004 |
| | 0.129(251) | 0.051(1369) |

The above table shows that PCR1/pM52 possesses PEPCase activity and that the effector sensitivity is characteristic to corn's PEPCase. Although not shown in the table, PEPCase activity was also measured on PCR1 grown in the presense of dioxane, which showed a negative value.

2. Eletrophoretic Characterization of Recombinant Plasmid Products (i) Experimental Procedure Respective cell-free extracts of PCR1 and PCR1/pM52 were subjected to polyacrylamide gel electrophoresis (PAGE), SDS-PAGE and activity staining of enzyme. After a comparative study of the experimental results, the molecular weight of corn PEPCase was estimated.

(ii) Results

After PAGE or SDS-PAGE, the activity staining and/or protein staining were conducted on the cell extracts. The activity staining revealed that PCR1/pM52 had a broad band below E. coli PEPCase.

3. Study on Reaction Between Cell-Free Extract and Corn PEPCase Antiserum (i) Experiment Dot-Immunoblotting technique[24] was employed for study on the reactivity of cell-free extract of PCR1/pM52 against corn PEPCase antiserum. In addition, cross-reactivity of the antiserum with various PEPCase derived from other species was also studied.

Specifically, a cell extract was spotted on a membrane filter and allowed to react with primary antibody, i.e., rabbit corn-PEPCase antiserum and subsequently with secondary antibody, i.e., sheep anti-rabbit IgG conjugated with peroxidase so that the secondary antibody may react with a coloring reagent under action of the peroxidase. The reactivity of the antigen to the primary antibody was determined on the basis of color strength of the spots. Quantitative analysis of the amount of the antigen or the titer determination of the primary antibody was also made using a dilution series of the antigen or the primary antibody.

The above procedure was conducted using Bio-Dot ™ apparatus (BIO-RAD) and in accordance with the manual for manipulation provided by the manufacturer, but with some modification. Such modified procedure is described below.

A nitrocellulose filter was immersed in TBS buffer (50 mM Tris-HCl, pH 7.4, 0.2 M NaCl), placed on a filter paper for five minutes, and set in the apparatus. Each well in the apparatus was washed using TBS buffer with suction. After disconnecting the suction from the apparatus, 1 µl of cell-free extract (antigen solution) was spotted, gravitationally filtered and then suction-dried. A blocking solution comprising 3% (w/v) gelatin (Bio-Rad, EIA grade) plus TBS was added to each well, gravitationally filtered over 30 minutes, and suction-dried. To each well was added under suction 200 µl of TTBS buffer comprising 0.05% (v/v) Tween 20 plus TBS. The primary antibody (5 µl) was added thereto, gravitationally filtered for one hour, and suction-dried. The antibody was appropriately diluted with ABS buffer (1% gelatin/TBS) before use.

In a similar manner as mentioned above, each well and spot were washed three times with TTBS buffer (200 µl). The secondary antibody (100 µl) was then added thereto, filtered over 30 to 60 minutes, suction-dried, and washed three times with TTBS buffer (200 µl). In these processes an antigen-primary antibody-secondary antibody complex was fixed on the filter. The filter was immersed in a color developing solution which had been prepared by mixing, just before use, 4-chloro-α-naphthol (60 mg) in cold methanol (20 ml) and about 40% $H_2O_2$ (60 µl) in TBS (100 ml). When color was developed, the reaction was stopped by washing with water. The film was dried in the dark and photographed using a yellow filter.

(ii) Results

Dot-Immunoblotting mentioned above revealed that the product expressed by the plasmid pM52 was corn PEPCase.

4. Western Blotting Method[26]

(i) Experimental Procedure

Western blotting is the skillful method which has been developed to electrically transfer a band-pattern of proteins on SDS-PAGE to a protein-absorbing filter. The transferred and fixed proteins on the filter can be detected and identified by treating with both a primary antibody specific to a particular protein and a secondary antibody specific to the primary antibody, the secondary antibody being radiosensitively labeled or conjugated with a fluorescent substance or peroxidase so as to be easily detected. In addition, the molecular weight of particular protein can be determined by comparing the mobility of the protein on SDS-PAGE with that of a suitable molecular marker.

According to the above procedure, respective cell-free extracts of PCR1/pM and PCR1 and partially purified corn PEPCase were subjected to SDS-PAGE (7.5% gel, 80 mm×60 mm×1 mm) by the use of the minislab gel electrophoretic apparatus (ATTO).

After electrophoresis, the gel was immersed in a precooled transfer buffer (25 mM Tris-192 mM glycine/20% (v/v) methanol, pH 8.3) over 5 minutes and placed on a filter paper (Toyo No. 526), which had been dipped in the transfer buffer, with care so that air would not remain between the gel and the filter paper. A millipore filter (Millipore, GVHP) which had been dipped in the transfer buffer was then placed on the gel while paying attention so that no air would remain between the gel and the filter. Another filter paper similarly treated with the transfer buffer was overlaid on the filter, and the entirety was pinched with a pad and a holder, immersed in a transfer buffer (3 l) kept at about 4° C., and set in the transfer apparatus (Trans Blot TM System, Bio-Rad). Bubble was removed by up-and-down vibration of the apparatus. The proteins on the gel were allowed to transfer to the millipore filter over 2 to 3 hours when operated at 65V. Detection and identification of the proteins on the filter were conducted in a manner as detailed below.

The filter was immersed in a blocking solution and allowed to stand at room temperature for 30 to 60 minutes. The filter was then incubated for 1 to 2 hours in a primary antibody solution (70-fold dilution), washed with water (×1) and TTBS buffer (×2) over 10 minutes respectively. Subsequently, the filter was incubated for one hour in the secondary antibody solution and washed in the same manner as above. The washing was carefully performed because insufficient washing might yield vague test results due to non-specific bindings. The wet filter was drained well and immersed in a color developing solution. The colored filter thus obtained was washed with water. When the proteins and molecular weight marker proteins which had been transferred to the filter were to be seen, the filter was stained by an Amido Black reagent (0.1% Amido Black 10 , 5% acetic acid, 50% methanol).

(ii) Results

Figure 5:
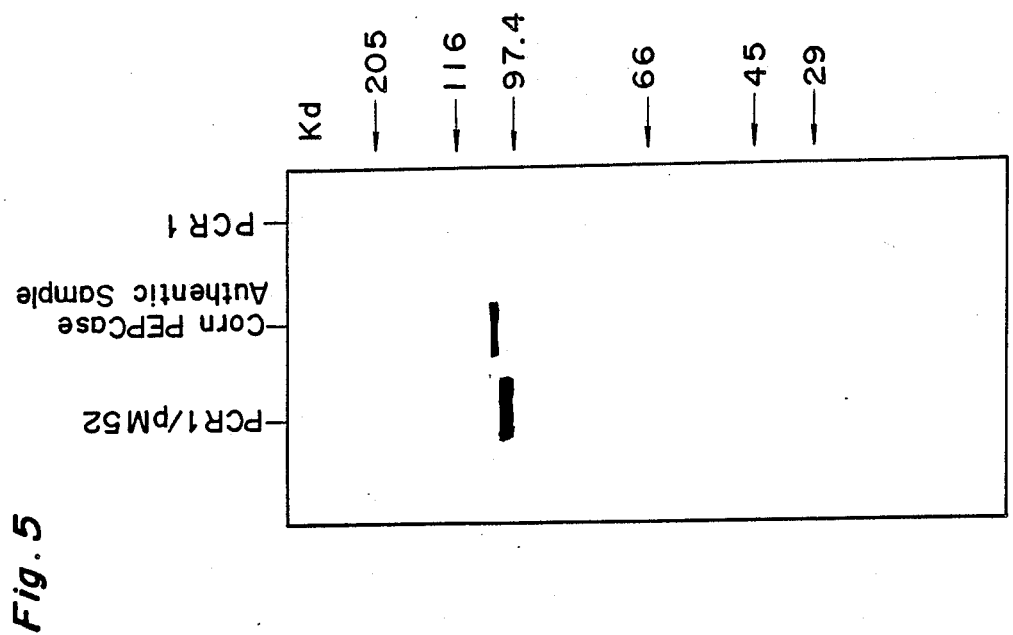
FIG. 5 illustrates the result of Western Blotting analysis of cell-free extracts of microorganisms including *Escherichia coli* transformed with plasmid pM52.

The result of Western blotting is presented in FIG. 5 of the accompanying drawing. In FIG. 5, PCR1/pM52 and corn PEPCase lanes show significant bands. The mobility of the former were, however, somewhat larger than the latter. From these data the molecular weight of the expressed product of cDNA derived from corn ppc was estimated to be about 90,000, being about 10,000 daltons smaller than the authentic PEPCase.

Bibliography (1) Uedan, K. F. and Sugiyama, T.; Plant Physiol., 57 906–910 (1976)
(2) Wong, K. F. and Davis, D. D.; Biochem. J., 131, 451–458 (1973)
(3) Hague, D. R. and Sims, T. L.; Plant Physiol., 66, 505–509 (1980)
(4) Sims, T. L.; J. Biol. Chem., 256, 8252–8255 (1981)
(5) Marie, S. and Sylia, L.; Photosynthetica, 17, 379–385 (1983)
(6) Nelson, T., Harpster, M. H., Mayfield, S. P. and Taylor, W. C.; J. Cell Biol., 98, 558–564 (1984)
(7) Sabe, H., Miwa, T., Kodaki, T., Izui, K., Hiraga, S. and Katsuki, H.; Gene, 31, 279–283(1984)
(8) Kissane, J. M. and Robin, E.; J. Biol. Chem., 233 184–188 (1958)
(9) Maniatis, T., Fritsch, E. F. and Sambrook, J.; "Molecular Cloning", p.197, Cold Spring Habor Laboratory
(10) Shigesada, K.; Saibo Kogaku (Cell Technology), 2, 616–626 (1983)
(11) Okayama, H. and Berg, P.; Mol. Cell. Biol., 2, 161–170 (1982)
(12) Okayama, H. and Berg, P.; Mol. Cell. Biol., 3, 280–289 (1983)
(13)=(10)
(14) Birnboim, H. C. and Doly, J.; Nucl. Acids Res., 7, 1513–1523 (1979)
(15) Kusnner, S. R.; "Genetic Engineering", p.17, Elsevier (1978)

(16) Bolivar, F. and Backman, K.; "Methods in Enzymology", 68, p.253, Academic Press, New York (1979)

(17) Takagi, Y.; "Idenshi-sosa Manual (Gene Manipulation Manual)", pp. 47-49, Kodan-sha (1982)

(18) Sanger, F.; Science, 214, 1205-1210

(19) Messing, J., Crea, R. and Seeburg, P. H.; Nucl. Acids Res., 9, 309-321 (1981)

(20) Yoshinaga, T., Izui, K. and Katsuki, H.; J. Biochem., 68, 747-750 (1970)

(21) Katagiri, F.; special study thesis in 1983 (1984)

(22) Izui, K., Nishikido, T., Ishihara, K. and Katsuki, H.; J. Biochem., 68, 215-226 (1970)

23) Lowry, O. H., Rosebrough, N. J., Farr, A. L. and Rondall, R. J.; J. Mol. Biol., 193, 265-275

(24) Ishijima, S., Taguchi, M., Hirai, K., Nanba, Y., Hanaoka, M., Izui, K. and Katsuki, H.; Seikagaku (Biochemistry), 55, 815 (1983)

(25) Personal communication

(26) Towbin, H., Staehelin, T. and Gordon, J.; Proc. Natl. Acad. Sci., USA, 76, 4350-4354 (1979)

What we claim is:

1. A microorganism which is *Escherichia coli* K12/pM52.
2. The expression vector pM52.
3. A process for producing an enzymatically active corn phosphoenolpyruvate carboxylase, which comprises:
   cultivating in a liquid media *Escherichia coli* transformed with the expression vector pM52, and
   recovering the expressed carboxylase from said transformed *E. coli.*

* * * * *